United States Patent [19]

Coates

[11] 4,257,961

[45] Mar. 24, 1981

[54] PURIFICATION OF TETRAHYDROFURAN

[75] Inventor: John S. Coates, Newark, Del.

[73] Assignee: E. I. Du Pont de Nemours and Company, Wilmington, Del.

[21] Appl. No.: 158,610

[22] Filed: Jun. 11, 1980

[51] Int. Cl.$^3$ .......................................... C07D 307/08
[52] U.S. Cl. ................................................ 260/346.11
[58] Field of Search ................................... 260/346.11

[56] References Cited

U.S. PATENT DOCUMENTS

| 3,560,576 | 2/1971 | Kirchner | 260/635 |
| 3,650,985 | 3/1972 | Kirchner | 252/431 |
| 3,692,859 | 9/1972 | Cottle | 260/346.11 X |
| 3,726,905 | 4/1973 | Coates et al. | 260/346.11 |
| 4,093,633 | 6/1978 | Tanabe et al. | 260/346.11 |

Primary Examiner—Richard Raymond

[57] ABSTRACT

The amounts of methacrolein-, dihydrofuran-and aldehydic impurities in THF made from acetylene and formaldehyde can be significantly reduced by hydrogenating them during an interval in the multi-stage distillation THF refining procedure.

4 Claims, No Drawings

PURIFICATION OF TETRAHYDROFURAN

DESCRIPTION

1. Technical Field

This invention relates to an improvement in a process for refining crude tetrahydrofuran (THF).

2. Background Art

THF is a commodity in the chemical industry, widely used as a solvent and as an intermediate in the preparation of various polymeric glycols which are useful in preparing polyurethanes.

One of the several methods used to commercially prepare THF is a four-step process which employs acetylene and formaldehyde as starting materials. In step 1 of the process, acetylene and formaldehyde are reacted to form 1,4-butynediol, using a copper-acetylide complex as the catalyst. This reaction is described in U.S. Pat. Nos. 3,560,576 and 3,650,985, both to J. R. Kirchner.

In step 2, butynediol formed in the first step is catalytically hydrogenated to 1,4-butanediol, using Raney nickel as the catalyst. This procedure is descirbed in British Patent No. 1,242,358.

In step 3, butanediol from step 2 is catalytically dehydrated and cyclized to THF using sulfuric acid as the catalyst, as described in U.S. Pat. No. 3,726,905 to J. S. Coates and V. J. Reilly.

Crude THF produced in step 3 is then refined in step 4, which is a multi-stage distillation, as described in U.S. Pat. No. 4,093,633 to Tanabe, et al.

The THF produced in step 3 of the process contains methacrolein, dihydrofurans (2,3- and 2,5-), propionaldehyde and butyraldehydes (normal and isomeric), impurities whose presence causes color formation in polymeric glycols made from the THF. It is difficult to remove these compounds effectively in the step 4 distillation because of the proximity of their boiling points to that of THF itself. A need therefore exists for a way of separating these impurities from THF easily and inexpensively.

DESCRIPTION OF THE INVENTION

It has now been found, according to the invention, that these impurities can be easily and effectively separated from crude THF by hydrogenating the crude THF during an interval in the step 4 multi-stage distillation and then continuing the distillation. This hydrogenation converts the methacrolein and butyraldehydes to compounds which are easily removed in the final stage or stages of distillation, and simultaneously converts the dihydrofuran impurities to THF itself.

The hydrogenation can be carried out during any interval of the step 4 distillation process, but is preferably done at a point where the THF is dry, i.e., where most of the water has been removed and only an insignificant amount remains. In the three-stage distillation often used in step 4, hydrogenation is conveniently conducted during the interval in which the THF passes from the second distillation column to the third.

Hydrogenation is carried out in a separate reactor positioned in the THF line and packed in a conventional manner with Raney nickel catalyst. Hydrogen is fed into the reactor at a rate of 0.00005–0.0005 m³/sec (0.1–1 cfm), preferably 0.0004–0.0005 m³/sec (0.8–1 cfm) and is held at a pressure of 172–1379 kPa gauge (25–200 psig), preferably 483–621 kPa gauge (70–90 psig). The temperature of the THF (measured as it enters the reactor) is maintained in the range 25°–100° C., preferably 70°–90° C.

Hydrogenation is conducted in continuous fashion, with crude, preferably dry, THF being fed into the reactor from one distillation column and reactor effluent being fed into the next column. THF is fed into the reactor at a rate which will give a residence time in the reactor of 1–16 minutes, preferably 7–10 minutes.

BEST MODE

THF from the second column of a three-column distillation refining train, at a temperature of about 100° C., was fed upwardly at the rate of about 10 parts by volume per minute into a reactor containing 100 parts by weight of foraminous Raney nickel. Hydrogen pressure in the reactor was maintained at 690 kPa gauge (100 psig). Effluent from the reactor was fed directly into the third distillation column.

The level of impurities in the feed to the reactor, and in the final product from the third distillation column, was determined with a gas chromatograph equipped with a flame-ionizing detector, using a column (supplied by Supelco, Inc.) packed with Ucon 550 XLB, a polypropylene glycol supplied by Union Carbide Co., supported on "Chromsorb P", sold by Hewlett-Packard, Inc.

The results are as follows:

| Impurity | Amount in Feed ppm | Amount in Product ppm |
| --- | --- | --- |
| Propionaldehyde | 23 | 3 |
| Isobutyraldehyde | 22 | 6 |
| n-Butyraldehyde | 38 | 8 |
| 2,3-Dihydrofuran | 44 | 4 |
| Methacrolein | 9 | 0.7 |

INDUSTRIAL APPLICABILITY

The process of the invention can be used in the commercial manufacture of THF from acetylene and formaldehyde.

I claim:

1. In the multi-stage distillation refining of tetrahydrofuran (THF) made from acetylene and formaldehyde, a method of reducing the concentration of the methacrolein, dihydrofuran, propionaldehyde and butyraldehyde impurities, the method comprising catalytically hydrogenating dry THF from one of the distillation stages at a temperature of 25°–150° C. and a hydrogen pressure of 172–1379 kPa gauge, using Raney nickel as the catalyst, and then separating THF and the resulting chemically modified impurities by subsequent distillation.

2. The process of claim 1 in which hydrogenation is carried out at a temperature of 70°–90° C.

3. The process of claim 1 in which hydrogenation is carried out at a hydrogen pressure of 483–621 kPa gauge.

4. In the three-stage distillation refining of THF made from acetylene and formaldehyde, a method of reducing the concentration of the methacrolein, dihydrofuran, propionaldehyde and butyraldehyde impurities, the method comprising continuously catalytically hydrogenating dry THF from the second distillation column at a temperature of 70°–90° C. and a hydrogen pressure of 483–621 kPa gauge, using Raney nickel as the catalyst, and then separating THF and the resulting chemically modified impurities in the third distillation column.

* * * * *